US006428991B1

(12) United States Patent
Fukuoka et al.

(10) Patent No.: US 6,428,991 B1
(45) Date of Patent: Aug. 6, 2002

(54) PROCESS FOR PRODUCING LEVODIONE

(75) Inventors: Masatsuka Fukuoka, Shizuoka-ken; Koki Hiraga, Kakegawa; Toru Sekihara, Fukuroi, all of (JP)

(73) Assignee: Roche Vitamins Inc., Parsippany, NJ (US)

( * ) Notice: Subject to any disclaimer, the term of this patent is extended or adjusted under 35 U.S.C. 154(b) by 0 days.

(21) Appl. No.: 09/628,077

(22) Filed: Jul. 28, 2000

(30) Foreign Application Priority Data

Aug. 2, 1999 (EP) .............................. 99115237

(51) Int. Cl.$^7$ ................................. C12P 7/26
(52) U.S. Cl. ...................... 435/148; 435/71.1; 435/132; 424/195.16
(58) Field of Search ...................... 435/41, 71.1, 289.1, 435/243, 183, 254.21, 254.22; 424/195.16

(56) References Cited

U.S. PATENT DOCUMENTS

| 3,960,966 A | | 6/1976 | Widmer et al. |
| 4,072,715 A | | 2/1978 | Boguth et al. |
| 4,156,100 A | * | 5/1979 | Boguth et al. |

FOREIGN PATENT DOCUMENTS

| EP | 0864600 A1 | * | 9/1998 |

OTHER PUBLICATIONS

Nelis, et al., "Microbial Production of Carotenoids," in *Biotechnology of Vitamins, Pigments and Growth Factors*, Ed. Erick J. Vandamme, Elsevier Applied Science, London and New York, pp. 71–73 (1989).
Powell, "Immobilized Biocatalyst Technology," *Microbial Enzymes and Biotechnology*, 2nd Edition, Ed. William M. Fogarty and Catherine T. Kelly, Elsevier Applied Science, London and New York, pp. 369–394 (1990).
Derwent English language abstract of JP 61265/1994.

* cited by examiner

Primary Examiner—Leon B. Lankford, Jr.
Assistant Examiner—Ruth Davis
(74) Attorney, Agent, or Firm—Bryan Cave LLP

(57) ABSTRACT

The present invention provides a process for producing (6R)-2,2,6-trimethylcyclohexene-1,4-dione. This process includes contacting, in a reactor, 2,6,6-trimethyl-2-cyclohexene-1,4-dione with a yeast selected from the group consisting of *Saccharomyces rouxii* (*Zygosaccharomyces rouxii*), *Saccharomyces delbrueckii* (*Saccharomyces unisporus, Tonilaspora delbrueckii*), *Saccharomyces willianus, Zygosaccharomyces bailii, Candida tropicalis,* functional equivalents, subcultures, mutants, and variants thereof, in water, a water-miscible organic solvent, or a mixture of water and the water-miscible. organic solvent containing at least one assimilable carbon source; and isolating (6R)-2,2,6-trimethylcyclohexane-1,4-dione produced by the yeast from the reaction medium.

13 Claims, 1 Drawing Sheet

PROCESS FOR PRODUCING LEVODIONE

FIELD OF THE INVENTION

The present invention relates to the microbial production of (6R)-2,2,6-trimethylcyclohexane-1,4-dione (hereinafter referred to as levodione), a useful intermediate in the production of carotenoids, such as (3R,3'R)-zeaxanthin. More particularly, the present invention relates to a process for producing levodione of high purity and in high yield by the catalytic reaction of 2,6,6-trimethyl-2-cyclohlexene-1,4-dione (hereinafter referred to as ketoisophorone) with a specific yeast.

BACKGROUND OF THE INVENTION

Levodione has previously been prepared through the reduction of the carbon-carbon double bond in ketoisophorone by contacting the ketoisophorone with baker's yeast, such as *Saccharomyces cervisiae,* which functions as an enantioselective biocatalyst (Biotechnology of Vitamins, Pigments and Growth Factors, Ed. Erick J. Vandamme, page 71, Elsevier Applied Science, London and New York). However, baker's yeast is not suitable for use in the industrial production of levodione because the yields are too low. In addition, the use of baker's yeast in the production of levodione is inefficient because the yeast cells cannot be reused because of the short lifetime of the reaction activity of the yeast. In addition, a complicated purification process is necessary when baker's yeast is used in the production process because it is difficult to separate the yeast from the culture solution after the catalytic reaction.

SUMMARY OF THE INVENTION

One embodiment of the invention is a process for producing (6R)-2,2,6-trimethylcyclohexane-1,4-dione. This process includes contacting, in a reactor, 2,6,6-trimethyl-2-cyclohexene-1,4-dione with a yeast selected from the group consisting: of *Saccharomyces rouxii* (*Zygosaccharomyces rouxii*), *Saccharomyces delbrueckii* (*Saccharomyces unisporus, Torulaspora delbrueckii*), *Saccharomyces willianus, Zygosaccharomyces bailii, Candida tropicalis,* functional equivalents, subcultures, mutants, and variants thereof, in water, a water-miscible organic solvent, or a mixture of water and the water-miscible organic solvent containing at least one assimilable carbon source; and isolating (6R)-2,2,6-trimethylcyclohexane-1,4-dione produced by the yeast from the reaction medium.

Another embodiment of the invention is a process for producing (6R)-2,2,6-trimethylcyclohexane-1,4-dione. This process includes contacting 2,6,6-trimethyl-2-cyclohexene-1,4-dione with a reaction medium containing yeast, an aqueous solvent, and at least one assimilable carbon source, wherein the yeast is selected from the group of *Saccharomyces rouxii* (*Zygosaccharomyces rouxii*), *Saccharomyces delbrueckii* (*Saccharomyces untisporus, Torulaspora delbrueckii*), *Saccharomyces willianus, Zygosaccharomyces bailii, and Candida tropicalis.* The (6R)-2,2,6-trimethylcyclohexane-1,4-dione produced by the yeast is then isolated from the reaction medium.

A further embodiment of the invention is process for producing (6R)-2,2,6-trimethylcyclohexane-1,4-dione. This process includes entrapping yeast cells within a carrier made of a hydrophobic photo-crosslinkable resin having at least two ethylenic unsaturated linkages per molecule, wherein the yeast cells are selected from the group of *Saccharomyces rouxii* (*Zygosaccharomyces rouxii*), *Saccharomyces delbrueckii* (*Saccharomyces unisporus, Torulaspora delbrueckii*), *Saccharomyces willianus, Zygosaccharomyces bailii, and Candida tropicalis.* The resin is then irradiated with UV light to form a polymerized yeast carrier. The yeast in the yeast carrier is then preconditioned in a growth medium containing at least one assimilable carbon source, an assimilable nitrogen source, and inorganic salts. 2,6,6-trimethyl-2-cyclohexene-1,4-dione is then added to a reaction medium containing the preconditioned yeast cells from the previous step, an aqueous solvent, and at least one assimilable carbon source. Then, the (6R)-2,2,6-trimethylcyclohexane-1,4-dione produced by the yeast is isolated from the reaction medium.

DETAILED DESCRIPTION OF THE INVENTION

Figure 1:
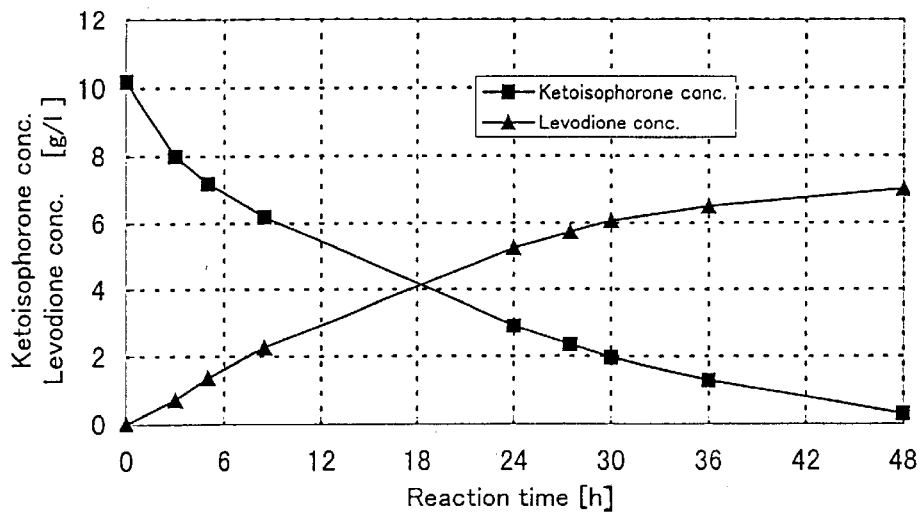
FIG. 1 is a graph showing the change in concentration of ketoisophorone and levodione during a reaction according to the present invention using *Zygosaccharomyces rouxii* HUT 7791 cells.

As a result of extensive studies to increase the yield of levodione produced from ketoisophorone and to overcome the aforementioned problems of the prior art, it has been found that certain yeast strains produce levodione much more efficiently from ketoisophorone than previously described.

The present invention provides a process for producing levodione by contacting, in a reactor, ketoisophorone with at least one kind of yeast which converts ketoisophorone into levodione. In the present invention, the yeast is selected from the following species: *Saccharomyces rouxi* (*Zygosaccharomyces rouxii*), *Saccharomyces delbrueckii* (*Saccharomyces unisporus, Torulaspora delbrueckii*), *Saccharomyces willianus, Zygosaccharomyces bailii, Candida tropicalis* and mixtures thereof. The yeast may also be a functional equivalent, subculture, mutant or variant of such a species. The mutant of a yeast used in the present invention can be induced by treating a wild type strain with a mutagen such as ultraviolet, x-ray or γ-ray irradiation, or by contact with nitrous acid or other suitable mutagen. A mutant may also be obtained by isolating a clone occurring by spontaneous mutation thereof, which may be effected by methods known per se by skilled artisans for such purposes. Many of these methods have been described in specialized publications, e.g., "Chemical Mutagens" edited by Y. Tajima, T. Yoshida and T. Kada, Kodansha Scientific Inc., Tokyo, Japan, 1973.

In the process of the present invention, the yeast species is combined with an aqueous solvent, i.e., water, a water-miscible organic solvent or a mixture of water and the water-miscible organic solvent, containing at least one assimilable carbon source. After completion of the reaction, levodione is isolated from the reaction medium.

The process; of the present invention also includes entrapping one of the above-described yeast species by certain techniques described below (see, e.g., Example 3) and using the so-immobilized yeast in the catalytic reaction to produce levodione of high purity in even higher yields compared to the prior art. This represents a preferred feature of the present invention.

Methods for immobilizing yeast are well known. See, for example, W. M. Fogarty, et al., Microbial Enzymes and Biotechnology, $2^{nd}$ Edition, Elsevier Applied Science, pp. 373–394 (1983), or Japanese Patent Publication No. 61, 265/1994. In the present invention, carriers for immobilizing yeast by an "entrapment method" include the following:

(i) High molecular weight polysaccharide gels, such as sodium alginate, potassium carrageenan, gelatin and agar, which are extracted from natural products;

(ii) Chitosan beads, which consist of high molecular weight polysaccharide derived from natural products;

(iii) Ceramic beads; and (iv) Hydrophobic photo-crosslinkable resins, which contain at least two ethylenic unsaturated linkages per molecule and are polymerized by irradiation.

Among the above-mentioned carriers, hydrophobic photo-crosslinkable resin polymerized by irradiation, i.e. (iv), is most preferably used in the present invention. Examples of hydrophobic photo-crosslinkable resins include the following:

(iv,a) Urethane adduct formed from the reaction between polypropylene glycol and (meth)acrylic acid;

(iv,b) Urethane adduct formed from the reaction between polyethylene glycol and (meth)acrylic acid;

(iv,c) Polyvinylalcohol and (iv,d) a mixture of the urethane adducts (iv,a) and (iv,b).

Such hydrophobic photo-crosslinkable resins are available commercially, such as for example, "BEL ENTG-3800" from Kansai Paint Co., Ltd., Hyogo-ken, Japan.

As used herein, "entrap," "entrapment," and "immobilize" are used interchangeably. These terms mean that the yeast cells are suspended in a carrier, but remain viable, are freely accessible to the reaction medium, including the ketoisophorone, and produce levodione therewith.

Ketoisophorone, used as the starting material or "substrate" in the process of the present invention, is a well-known substance, and can itself be readily synthesized by methods known from the literature, e.g. as reported in Widmer, et al., U.S. Pat. No. 3,960,966.

Any yeast having the ability to convert ketoisophorone into levodione and which belongs to the group of species consisting of *Saccharomyces rouxi* (*Zygosaccharomyces rouxii*), *Saccharomyces delbrueckii* (*Saccharomyces unisporus, Torulaspora delbrueckii*), *Saccharomyces willianus, Zygosaccharomyces bailii,* and *Candida tropicalis* may be used in the present invention. Furthermore, functional equivalents, subcultures, mutants and variants of these yeast species may also be used in the present process. Preferably at least one of the following deposited yeast is used in the present process:

*Saccharomyces rouxii* (*Zygosaccharomyces rouxii*) HUT 7191 (IFO 0494)

*Saccharomyces delbrueckii* HUT 7116 (*Saccharomyces unisporus* IFO 0298),

*Saccharomyces delbrueckii* (*Torulaspora delbrueckii*) HUT 7102,

*Saccharomyces willianus* HUT 7106,

*Zygosaccharomyces bailii* ATCC 11486 and

*Candida tropicalis* IFO 1403.

As noted above, functional equivalents, subcultures, mutants and variants of the above-identified yeast are also part of the present invention.

*Saccharomyces rouxii* (*Zygosaccharomyces rouxii*) HUT 7191 (IFO 0494) is the yeast most preferred for use in the process of the present invention.

*Saccharomyces rouxii* HUT 7191, *Saccharomyces delbrueckii* HUT 7116, and *Saccharomyces delbrueckii* HUT 7102 are listed in the HUT Catalogue, which issued in 1987. However, the HUT Catalogue which issued in September 1999 reclassifies the first and third of these microorganisms as *Zygosaccharomyces rouxii* HUT 7191 and *Torulaspora delbrueckii* HUT 7102, respectively, and no longer lists *Saccharomyces delbrueckii* HUT 7116. The IFO Catalogue, which issued in 1996 classifies "HUT 7116" as *Saccharomyces unisporus* IFO 0298.

The preferred yeast identified above have been deposited with at least one of the following depositories: American Type Culture Collection (ATCC), 10801 University Boulevard Manassas, Va.20100-2209, U.S.A., HUT Culture Collection Room, Department of Fermentation Technology, Hiroshima University and Institute for Fermentation (IFO), 17–85 Juso-honmachi 2-chome, Yodogawa-ku, Osaka, Japan. Each yeast is available from its depositary to anyone upon request.

The yeast may be "preconditioned" prior to use in the process by cultivating it in a growth medium containing an assimilable carbon source, an assimilable nitrogen source, inorganic salts, and other well-known supplements. The preconditioned yeast cells are then separated from the medium by any conventional process, such as centrifugation. The preconditioning cultivation of the yeast is generally carried out at a temperature range from 20° C. to 40° C., preferably from 25° C. to 30° C.; in a pH range from 3.0 to 6.0, preferably from 4.3 to 4.7; and for 6–48 hours, preferably for 20–30 hours, under aerobic conditions.

In the present invention, assimilable carbon sources include sucrose, sorbitol, glucose and the like, of which glucose is preferred. Assimilable nitrogen sources include, for example, ammonium sulfate, sodium nitrate, peptone, amino acids, corn steep liquor, malt extract, bran extract, yeast extract, and the like. Inorganic salts include, for example, magnesium sulfate, sodium chloride, calcium carbonate, dipotassium phosphate, and the like.

The process of the present invention is carried out in an aqueous solvent. As used herein, "aqueous solvent" means water, a water-miscible organic solvent, or a mixture: of water and the water-miscible organic solvent. The water-miscible organic solvent may be a lower ($C_{1-6}$) alkanol, such as for example, methanol, ethanol, or propanol. However, water is preferably used as the solvent.

The process is carried out at a temperature range from 20° C. to 40° C., preferably from 25° C. to 30° C. Narrower temperature ranges, however, for any combination of other reaction conditions, may be determined by the skilled artisan. The pH is from 3.0 to 6.0, preferably from 4.0 to 5.0. The reaction may be terminated 2 to 40 hours after its initiation. Preferably, the reaction is terminated after confirming that the ketoisophorone concentration in the reaction medium (i.e., the yeast, aqueous solvent, and carbon source) has reached a very low or even zero value using an analytical method such as gas chromatography. The initial ketoisophorone concentration is 0.3% to 2.0% by weight, preferably 0.9% to 1.0% by weight.

Examples of the assimilable carbon source, which must be present in the reaction medium as an energy source for the yeast to produce levodione from ketoisophorone, include sucrose, sorbitol, glucose or the like, of which glucose is preferred. The initial concentration of such a carbon source in the medium is 2.0% to 8.0% by weight, preferably 2.5% to 3.5% by weight.

The process of the present invention may be conducted in a batchwise, semi-continuous or continuous manner. In one embodiment of the present invention, the yeast is suspended in an aqueous solvent and the suspension is introduced into a reactor, such as for example, a fluidized bed reaction or a fixed bed reactor. Ketoisophorone and glucose are then dissolved in further solvent, and the solution is adjusted to a pH of 3.0 to 6.0, preferably 4.0 to 5.0, and added continuously to the suspension of yeast in the reactor. After starting aeration in the reaction medium, the addition of the solution of ketoisophorone and glucose to the yeast suspension in the reactor is continued, and the resulting solution is removed continuously from the reactor by filtration. The rates of addition and removal are adjusted to maintain about the same volume in the reactor. The catalytic reaction is carried out at a temperature range from 20° C. to 40° C., preferably from 25° C. to 30° C. Aqueous sulphuric acid or sodium hydroxide may be used to adjust the pH of the medium. The time during which the ketoisophorone reacts with the yeast may vary according to the prevailing conditions. However, the time may be predetermined by adjusting both the feeding rate (i.e., the rate at which the media containing ketoisophorone is introduced into the reactor) and the removal rate (i.e., the rate at which the ketoisophorone-depleted media is removed from the reactor) so that ketoisophorone in the reactor is continuously being depleted.

In another embodiment of the present invention, yeast, which is in a floating state in the aqueous solvent, or yeast in an immobilized state, may be used in a fluidized bed reactor or in a fixed bed reactor. If the activity of the yeast decreases, it may be easily reactivated in the immobilized form, and levodione may be produced in good yield using the yeast in spite of its previous repeated use in the catalytic reaction. Accordingly, using yeast in the immobilized form in the present invention may improve the productivity of levodione.

As noted above, the process of the present invention may be conducted using a fluidized bed reactor or a fixed bed reactor. In addition, when immobilized yeast are to be used for the first catalytic reaction with ketoisophorone, it is preferable that activation, i.e., preconditioning of the immobilized yeast be performed before the reaction. Such activation/preconditioning may be carried out by contacting the immobilized yeast with a suitable growth medium, as defined above, with bubbling and stirring under suitable conditions for growth of the yeast.

The following examples are provided to further illustrate the process of the present invention. These examples are illustrative only and are not intended to limit the scope of the invention in any way.

EXAMPLES

Example 1

Use of a Fluidized Bed Reactor

Ketoisophorone and glucose are dissolved in an aqueous solvent. The resulting solution and a culture of immobilized yeast are then introduced into the reactor. The catalytic reaction is initiated by aeration and agitation. The concentration of ketoisophorone is 0.3% to 2.0% by weight, preferably 0.9% to 1.0% by weight, and that of glucose 2.0% to 4.0% by weight, preferably 2.5% to 3.0% by weight. The catalytic reaction may be carried out in a temperature range from 20° C. to 40° C., preferably 25° C. to 30° C., and in a pH range from 3.0 to 6.0, preferably 4.3 to 4.7. The aeration rate (volume of air/volume of medium/minute: vvm) is 0.5 to 3 vvm, preferably 1 to 2 vvm. The reaction time may vary depending on the conditions. However, reaction is stopped about 8 to 10 hours after the initiation of the reaction, preferably after confirming that the amount of ketoisophorone has been depleted and the amount of levodione has been increased using standard methods for detecting levodione, as follows:

The concentrations of the levodione up to the completion of the reaction are analyzed by gas chromatography. A sample of the reaction mixture is removed and extracted with 3 ml of ethyl acetate by intensive agitation for 1 minute using a laboratory mixer HM-10 (Iuchi Co. Ltd., 2-6-4 Hamamati, Nihonbashi, Tokyo, Japan). After allowing the two phases of the mixture to separate after standing for a few minutes, 1 $\mu$l of the upper layer containing levodione was injected by HP7673 Auto Sampler (Agilent Technologies, P.O. Box #10395, Palo Alto, Calif. 94303) into HP GC 5890 series .(Agilent Technologies) as the main instrument of gas chromatography. The injected solution was gasified at 250° C. Part of the gas (split ratio 1:50) was transferred into a DB-WAX capillary column (30m×0.25mm, film 0.25 micron; J&W Scientific Incorporated, 91 Blue Ravine Road, Folsom, Calif., 95630-4714 USA) with 0.6 ml/l of $N_2$ carrier gas. The column temperature was increased at 4° C./minute from 40° C. until 65° C. and thereafter at 30° C./minute until 220° C. The levodione was allowed to flow out of the column after about 15.8 minutes retention time by increasing of the column temperature, although the levodione contained in the gas was retained in the column. The levodione was detected by a flame ion detector at 300° C., and the concentration calculated To isolate the levodione upon completion of the catalytic reaction, only the resulting solution is removed from the reactor, followed by washing the immobilized yeast with an aqueous solvent. Then, the levodione may be isolated from the combined solution and washings by conventional processes. (See, e.g., Example 4). Immobilized yeast may be reactivated by washing with a suitable wash solvent, and may be used repeatedly thereafter for further catalytic reaction.

Example 2

Use of a Fixed Bed Reactor

Immobilized yeast is placed into the reactor. Ketoisophorone and glucose are dissolved in the water or aqueous solvent and the pH of the solution is adjusted to a value from 3.0 to 6.0, preferably 5.0. The concentration of ketoisophorone is 0.3% to 2.0% by weight, preferably 0.9% to 1.0% by weight, and that of glucose 2.0% to 4.0% by weight, preferably 2.5% to 3.0% by weight. The resulting solution is introduced into the reactor for the reaction with the immobilized yeast. The catalytic reaction may be carried out at a temperature range from 20° C. to 40° C., preferably 25° C. to 30° C. The reaction time may vary depending on the conditions. The reaction is stopped 24–48 hours after initiation of the reaction, preferably after confirming that the amount of ketoisophorone has been depleted. The levodione isolation process after the termination of the catalytic reaction is the same as in Example 1.

Example 3

Process for Immobilizing Yeast Using Irradiation-Polymerized Hydrophobic Photo-Crosslinkable Resin as the Carrier A liquid-state mixture is prepared from: (a) a hydrophobic photo-crosslinkable resin, (b) a photo-polymerization initiator, such as benzoin, acetone, benzoinmethylether, naphthol or 2-hydroxy-2-methylpropiophenone ($C_6H_5COC(CH_3)_2OH$), (c) a solvent to dilute the hydrophobic photo-crosslinkable resin, such as petroleum benzine, benzene, hexane, ethylene glycol, or formaldehyde, and (d) yeast.

The mixture containing the components (a), (b), (c), and (d) is then dripped into an aqueous solvent containing a detergent, such as sodium lauryl sulfate or a glycerol fatty acid ester, to form solid beads, at which stage the diameter of the beads, which may vary, is about 0.1 mm to 5 mm, preferably about 0.5 mm to 3.0 mm. The beads are then irradiated at a wavelength of about 250 nm to 600 nm for 2 to 5 minutes. The ratio of the components (a):(b):(c):(d), by weight in the starting liquid-state mixture is normally 100:0.1–5:10–200:0.001–50, respectively, but it is not restricted thereto.

Example 4

Process for Purifying/isolating Levodione Obtained by the Catalytic Reaction of the Invention The solid impurities and yeast cells from the catalytic reaction of the invention are removed by filtering or centrifuging the mixture of the resulting solution and the washings. The resulting filtrate is then contacted with an adsorption resin, such as a hydrophobic resin. The adsorbed levodione is then eluted from the resin with a hydrophilic organic solvent, e.g. a lower alcohol such as methanol, ethanol, or acetone. Using such an approach, levodione of high purity may be obtained.

Examples of the hydrophobic resins used in the process of the present invention include modified crosslinked polystyrene (SP-207) and crosslinked polystyrene (SP-800 and SP-850) (Mitsubishi Chemical Co., Tokyo, Japan). Among these resins, SP-850 is preferred because its adsorption capacity for levodione per unit volume is extremely high. Levodione in a solvent may be efficiently adsorbed onto a hydrophobic adsorption resin by contacting the resin with a solution having a volume which is 10 to 20 times the volume of the resin. When conducting the elution step, it is preferred that methanol of twice the volume of the resin be used as the elution solvent. Levodione eluted from the hydrophobic adsorption resin is crystallized by concentrating the pooled eluate followed by cooling the resulting concentrated eluate. Then, the levodione crystals may be isolated by filtration or centrifugation and obtained in a high yield.

By means of the process of the present invention, levodione having a purity of more than 99% may be produced at a recovery rate of 70% to 80%.

Example 5

Screening of Yeast

Commercially available baker's yeast (Oriental Yeast Co., Ltd., Tokyo, Japan; used for comparative purposes) and the following yeast obtained from public depositories (ATCC, HUT or IFO) were used in the present Example:

*Saccharomyces cerevisiae* ATCC 7754 (also used for comparative purposes),
*Saccharomyces rouxii* (*Zygosaccharomyces rouxii*) HUT 7191 (IFO 0494),
*Saccharomyces delbrueckii* HUT 7116 (*Saccharomyces unisporus* IFO 0298),
*Saccharomyces delbrueckii* (*Torulaspora delbrueckii*) HUT 7102,
*Saccharomyces willianus* HUT 7106,
*Zygosaccharomyces bailii* ATCC 11486,
*Candida tropicalis* EFO 1403

Each yeast was separately cultivated in a medium containing glucose, polypeptone, and yeast extract at 30° C. for 45 hours. Then, the yeast cells in each culture were collected by centrifugation.

In each case, collected yeast cells were suspended in ion exchanged water at a concentration of 80 g/l, and the pH of the aqueous solvent was adjusted to 4.2. In a separate operation, ketoisophorone and glucose were dissolved in ion exchanged water, both at a concentration of 17 g/l, and the pH of the aqueous solvent was adjusted to 4.2. The yeast suspension was mixed with the aqueous solvent containing the ketoisophorone and glucose in a volume ratio of 1:1. The reaction was carried out at 30° C. for 16 hours. Upon completion of the reaction, the concentration of levodione in each culture was determined by gas chromatography, from which the levodione production rate per unit yeast was calculated. The levodione production results are shown in Table 1.

TABLE 1

| Yeast used for screening | Levodione production rate (g/kg yeast cells/h) |
|---|---|
| Baker's yeast (Oriental Yeast Co., Ltd. Tokyo, Japan) | 8.8 |
| *Saccharomyces cerevisiae* ATCC 7754 | 9.8 |
| *Saccharomyces rouxii* (*Zygosaccharomyces rouxii*) HUT 7191 (IFO 0494) | 25.7 |
| *Saccharomyces delbrueckii* HUT 7116 (*Saccharomyces unisporus* IFO 0298) | 16.7 |
| *Saccharomyces delbrueckii* (*Torulaspora delbrueckii*) HUT 7102 | 16.0 |
| *Saccharomyces willianus* HUT 7106 | 14.8 |
| *Zygosaccharomyces bailii* ATCC 11486 | 12.6 |
| *Candida tropicalis* IFO 1403 | 10.5 |

From these results, it is clear that all experimental yeast strains used in the present invention produce levodione at a higher rate ($\geq 10.5$, as high as 25.7) compared to baker's yeast (8.8) and *Saccharomyces cerevisiae* ATCC 7754 (9.8).

Example 6

Catalytic Reaction Using Immobilized Yeast

*Saccharomyces rouxii* (*Zygosaccharomyces rouxii*) HUT 7191 (IFO 0494) and baker's yeast were cultivated separately for 24 hours at 30° C. using a stirred fermentor in a medium containing yeast extract (0.5% wt), polypeptone (1.0% wt), glucose (2.0% wt), $KH_2PO_4$ (0.5% wt) and $MgSO_4$ (0.2% wt) using a stirred fennentor. Because the glucose was depleted by the yeast cells in a growth phase about 12 hours after initiation of cultivation, glucose was added at a constant rate thereafter. The cells were collected from the culture by centrifugation and then suspended in ion exchanged water at a concentration of 100 g/l. A mixture of photo-crosslinkable resin (ENTG-3800) containing para-benzoquinone at 200 ppm had been prepared in advance and stored at room temperature for more than one week before use. The mixture of resin and parabenzoquinone, calcium alginate solution (1.8% by weight), the cell suspension, and 2-hydroxy-2-methylpropiophenone were mixed in a weight ratio of 55.5:22.2:22.2:0.1, respectively. The mixture was dripped into calcium chloride solution (3.0% by weight) through a syringe needle to produce solid beads having a diameter of about 3 mm. The beads were separated from the calcium chloride solution, and were immediately irradiated with ultraviolet rays (360 nm) for 3 minutes. After irradiation, the beads were washed with ion exchanged water.

A vertically elongated bubble tower reactor (5 liter) with baffle plates was used for each reaction. The reactor was packed with 800 g of the respective immobilized yeast. A solution containing 3.5 immobilized yeast volumes, yeast extract (0.1% wt), glucose (2.0% wt), $KH_2PO_4$ (0.2% wt), and $MgSO_4 7H_2O$ (0.1% wt) was added to the reactor and aeration was begun at a rate of 7.0 l/minute to activate the yeast. The temperature of the immobilized yeast and the activation solution was maintained at 30° C. and the pH was maintained at 4.5 by addition of aqueous sodium hydroxide solution during activation. The activation was completed after 24 hours, and only the activation solution was removed from the reactor. Then, 35 g of ketoisophorone and 75 g of glucose were added to the reactor, and the volume was brought to 3.5 l with ion exchanged water. Aeration was begun at a rate of 7.0 l/minute, and the catalytic reaction was initiated. The temperature of the immobilized yeast and the reaction mixture was maintained at 30° C. and the pH was maintained at 4.5 with 4.5N sodium hydroxide solution during the fermentation.

FIG. 1 shows the time course of the change in concentration of ketoisophorone and levodione in the reaction solution using immobilized i Saccharomyces rouxii (*Zygosaccharomyces rouxii*) HUT 7191.

Upon completion of the reaction, the reaction solution was removed and ketoisophorone and glucose were added to the reactor to perform the catalytic reaction once again. The reaction was repeated 10 times in the same manner.

Figure 2:
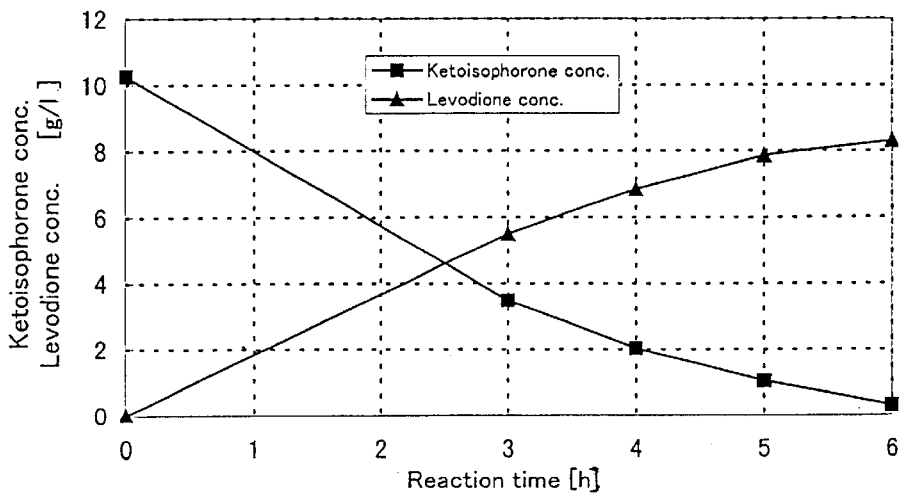
FIG. 2 is a graph showing the change in concentration of ketoisophorone and levodione during a process analogous to the present invention whereby baker's yeast, rather than one of the selected yeasts mentioned above, was used for comparative purposes.

For comparison, FIG. 2 shows the shifts in concentrations of ketoisophorone and levodione in the reaction solution using baker's yeast under the same conditions as described above.

Subsequently, after each fermentation run, the reaction solution was removed from the reactor and 3.5 immobilized yeast volumes of water (wash solvent) was added thereto and aeration was performed at a rate of 7.0 l/minute for 10 minutes to wash the immobilized yeast. The wash solvent was extracted thereafter, then ketoisophorone and glucose were added to the reactor to perform the catalytic reaction again. The catalytic reaction and the washing of the immobilized yeast were repeated 10 times in the same manner (10 cycles).

Figure 3:
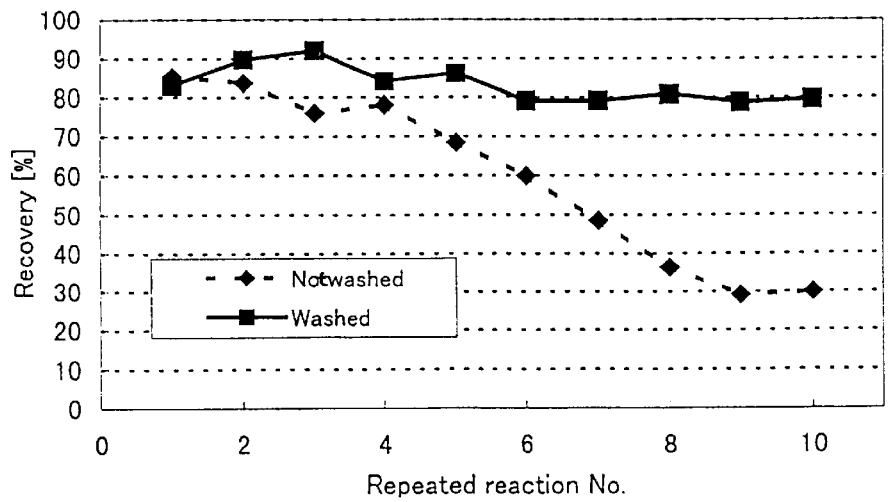
FIG. 3 is a graph showing the effect on levodione recovery of washing the immobilized yeast between each fermentation run.

FIG. 3 shows the shifts in recoveries of levodione to the added ketoisophorone from continuous fermentation using *Saccharomyces rouxii* (*Zygosaccharomyces rouxii*) HUT 7191, with or without incorporating a washing step.

Example 7

Industrial Scale Production of Levodione

*Saccharomyces rouxii* (*Zygosaccharomyces rouxii*) HUT 7191 (IFO 0494) was cultivated and a large amount of immobilized yeast was prepared by the same method as described in Example 6.

A vertically elongated bubble tower reactor with baffle plates (1 $m^3$) was used for the catalytic reaction. The reactor was packed with 230 kg of immobilized yeast prepared in advance. A solution of 3.5 immobilized yeast volumes which contained yeast extract (0.1 wt %), glucose (2.0 wt %), $KH_2PO_4$ (0.2 wt %), and $MgSO_4 7H_2O$ (0.1 wt %) was added thereto and aeration was begun at a rate of 0.4 $Nm^3$/minute to activate the yeast. The temperature of the immobilized yeast and the solution was maintained at 30° C. and the pH at 4.5 (with sodium hydroxide solution) during the activation. The activation was completed after 24 hours, and the activating solution was removed from the reactor. Then, 9 kg of ketoisophorone and 30 kg of glucose were added to the reactor and the volume was brought to 1000 l with ion exchanged water. Aeration was begun at a rate of 0.4 $Nm^3$/minute, and the catalytic reaction was initiated. The temperature of the immobilized yeast and the solution was maintained at 30° C. and the pH at 4.5 (with sodium hydroxide solution) during the reaction.

The reaction was completed once the amount of ketoisophorone had been depleted, and the resulting solution was removed from the reactor. Then, 3.5 immobilized yeast volumes of water was added to the reactor and aeration was performed at a rate of 0.4 $Nm^3$/minute for 15 minutes to wash the immobilized yeast. After the wash solvent had been discharged, the same amounts set forth in Example 6 of ketoisophorone and glucose were added to the reactor to carry out the reaction again. The reaction time was usually about 8 hours. However, if fermentation was carried out continuously more than 20 times, the production activity of the yeast declined, i.e., reaction time of more than 10 hours resulted in a decrease in production efficiency. Therefore, activation of immobilized yeast was performed by the same method set forth in Example 6 every 20 fermentation runs. As a result, the activity of the yeast did not decline despite the immobilized yeast having been repeatedly used for the catalytic reaction 100 times.

Purification of levodione was carried out by crystallizing levodione with mixtures of the resultant solution and the extracted wash solvent. The obtained mixtures were filtered by ultrafiltration, the filtration area being 5 $m^2$. The inflow rate was set at 250 l/hour. The filtrate was loaded onto a 200 l column filled with 150 l of hydrophobic adsorption resin SEPABEADS SP-850 (Mitsubishi Chemical Co., Tokyo, Japan) at a rate of 200 l/hour to adsorb levodione, ketoisophorone, and byproducts such as actinol. For one adsorption operation, 3,000 l of filtrate were applied to the resin. The resin adsorbing levodione, ketoisophorone, and byproducts in the column was heated to 50° C., and methanol solution, preheated to 50° C., was added to the column at a rate of 200 l/hour to elute levodione, ketoisophorone and byproducts.

For one elution operation, 200 l of methanol were applied to the resin. The methanol solution containing levodione, ketoisophorone, and byproducts was concentrated 6-fold using a concentrator at 60° C. under reduced pressure. The concentrate containing levodione, ketoisophorone, and byproducts was cooled to 5° C. and maintained at this temperature for more than 12 hours to crystallize levodione. The ketoisophorone and byproducts remained dissolved in methanol. The crystallized levodione was collected by filtration, washed with methanol to remove superficial ketoisophorone and byproducts, then dried. The production process was thereby completed, and levodione crystals having purity of more than 99% were obtained.

Using the above-described method, the reaction for producing levodione was repeated 100 times. Approximately 500 kg of levodione with an overall yield, based on the employed ketoisophorone, of about 70% and having a purity of more than 99% was produced.

Example 8

Evaluation of the Levodione Productivity of Yeast in the Immobilized Form

A comparison of the levodione productivity of baker's yeast with that of *Saccharomyces rouxii*

(*Zygosaccharomyces rouxii*) HUT 7191 (IFO 0494), which has a very high ability to produce levodione under free cell conditions, was performed, whereby both yeasts were in the immobilized state. The method of measuring the activities of immobilized yeast was as follows:

Immobilized yeast was prepared by the same method as described in Example 5, and activation was conducted. Ketoisophorone and glucose were dissolved in ion exchanged water to a final concentration of 10 g/l and 50 g/l, respectively, and the pH was adjusted to 4.5. The immobilized yeast (30 g) was suspended in the ketoisophorone and glucose mixture (30 ml) prepared beforehand and the reaction was initiated at 30° C. The reaction was completed when the ketoisophorone had been depleted. Levodione concentrations in the reaction solution were analyzed by gas chromatography. The productivity (g levodione/kg, yeast/h) of levodione by each yeast was then evaluated from the results, which is presented in Table 2 below:

TABLE 2

| Yeast | Productivity |
| --- | --- |
| Baker's yeast (Oriental Yeast Co., Ltd., Tokyo, Japan) | 0.69 |
| *Saccharomyces rouxii* (*Zygosaccharomyces rouxii*) HUT 7191 (IFO 0494) | 4.88 |

The invention being thus described, it will be obvious that the same may be varied in many ways. Such variations are not to be regarded as a departure from the spirit and scope of the invention and all such modifications are intended to be included within the scope of the following claims.

What is claimed is:

1. A process for producing (6R)-2,2,6-trimethylcyclohexane-1,4-dione at a rate of at least 10.5 g/Kg yeast/hour, comprising contacting, in a reactor, 2,6,6-trimethyl-2-cyclohexene-1,4-dione with a yeast selected from the group consisting of *Saccharomyces rouxii* (*Zygosaccharomyces rouxii*), *Saccharomyces delbrueckii* (*Saccharomyces unisporus, Torulaspora delbrueckii*), *Saccharomyces willianus, Zygosaccharomyces bailii, Candida tropicalis,* and mutants thereof, in water, a water-miscible organic solvent, or a mixture of water and the water-miscible organic solvent containing at least one assimilable carbon source; and isolating (6R)-2,2,6-trimethylcyclohexane-1,4-dione produced by the yeast from the reaction medium.

2. A process according to claim 1 further comprising cultivating the yeast prior to the contacting step in a growth medium containing an assimilable carbon source, an assimilable nitrogen source, and inorganic salts; and separating the yeast cells from the growth medium.

3. A process according to in claim 1 wherein the yeast is selected from the group consisting of *Saccharomyces rouxii* (*Zygosaccharomyces rouxii*) HUT 7191 (IFO 0494), *Saccharomyces delbrueckii* HUT 7116 (*Saccharomyces unisporus* IFO 0298), *Saccharomyces delbrueckii* (*Torulaspora delbrueckii*) HUT 7102, *Saccharomyces willianus* HUT 7106, *Zygosaccharomyces bailii* ATCC 11486, *Candida tropicalis* IFO 1403, and mutants thereof.

4. A process according to claim 3 wherein the yeast is *Saccharomyces rouxii* (*Zygosaccharomyces rouxii*) HUT 7191 (IFO 0494).

5. A process according to claim 1 wherein the yeast is an immobilized yeast.

6. A process according to claim 5 comprising entrapping the yeast, prior to the contacting step, in a hydrophobic photo-crosslinkable resin having at least two ethylenic unsaturated linkages per molecule, and polymerizing the resin by irradiation.

7. A process according to claim 1 wherein the 2,6,6-trimethyl-2-cyclohexene-1,4-dione is contacted with the yeast at a temperature of from 20° C. to 40° C. at a pH of from 3.0 to 6.0.

8. A process according to claim 7 wherein the 2,6,6-trimethyl-2-cyclohexene-1,4-dione is contacted with the yeast at a temperature of from 25° C. to 30° C. at a pH of from 4.0 to 5.0.

9. A process according to claim 1 wherein the reactor is a fluidized bed reactor or a fixed bed reactor.

10. A process for. producing (6R)-2,2,6-trimethylcyclohexane-1,4-dione at a rate of at least 10.5 g/kg yeast/hour, comprising:

(a) contacting 2,6,6-trimethyl-2-cyclohexene-1,4-dione with a reaction medium comprising yeast, an aqueous solvent, and at least on 6 assimilable carbon source, wherein the yeast is selected from the group consisting of *Saccharomyces rouxii* (*Zygosaccharomyces rouxii*), *Saccharomyces delbrueckii* (*Saccharomyces unisporus, Torulaspora delbrueckii*), *Saccharomyces willianus, Zygosaccharomyces baili,* and *Candida tropicalis;* and (b) isolating (6R)-2,2,6-trimethylcyclohexane-1,4dione produced by the yeast from the reaction medium.

11. A process according to claim 10 wherein the aqueous solvent is selected from the group consisting of water, a water-miscible organic solvent, and a mixture of water and the water-miscible organic solvent.

12. A process according to claim 10 further comprising, prior to the contacting step, entrapping the yeast in a hydrophobic, photo-crosslinkable resin having at least two ethylenic unsaturated linkages per molecule and polymerizing the resin by irradiation with UV light to immobilize the yeast in the resin.

13. A process for producing (6R)-2,2,6-trimethylcyclohexane-1,4-dione at a rate of at least 10.5 g/kg yeast/hour,comprising:

(a) entrapping yeast cells within a carrier comprising a hydrophobic photo-crosslinkable resin having at least two ethylenic unsaturated linkages per molecule, wherein the yeast is selected from the group consisting of *Saccharomyces rouxii* (*Zygosaccharomyces rouxii*), *Saccharomyces delbrueckii* (*Saccharomyces unisporus, Torulaspora delbrueckii*), *Saccharomyces willianus, Zygosaccharomyces bailii,* and *Candida tropicalis;*

(b) irradiating the resin with UV light to format a polymerized yeast carrier;

(c) adding (6R)-2,2,6-trimethylcyclohexane-1,4-dione to a reaction medium comprising the preconditioned yeast cells from step (c), and aqueous solvent, and at least one assimilable carbon source; and (d) isolating (6R)-2,2,6-trimethylcyclohexane-1,4-dione produced by the yeast from the reaction medium.

* * * * *

UNITED STATES PATENT AND TRADEMARK OFFICE
CERTIFICATE OF CORRECTION

PATENT NO. : 6,428,991 B1
DATED : August 6, 2002
INVENTOR(S) : Masatsuka Fukuoka et al.

It is certified that error appears in the above-identified patent and that said Letters Patent is hereby corrected as shown below:

Title page,
Item [75], Inventors, please change "Shizuoka-ken" to -- Shizuoka-Ken --; please change "Kakegawa" to -- Kakegawa-Shi --; and please change "Fukuroi" to -- Fukuroi-shi --;
Item [57], ABSTRACT,
Line 2, please change "(6R)-2,2,6-trimethylcyclohexene-1,4-dione" to -- (6R)-2,2,6-trimethylcyclohexane-1,4-dione --;
Line 7, please change "*Tonilaspora*" to -- Torulaspora --;
Line 11, please delete the period after "water-miscible";

Column 12,
Line 23, please change "on 6" to -- one --;
Line 28, please change "*baili*" to -- *bailii* --;
Line 29, please change "4dione" to -- 4-dione --;
Line 54, please add -- (c) preconditioning the yeast cells in a growth medium containing at least one assimilable carbon source, an assimilable nitrogen source, and inorganic salts --
Line 55, please change "(c)" to -- (d) --.
Line 59, please change "(d)" to -- (e) --.

Signed and Sealed this

Thirtieth Day of March, 2004

JON W. DUDAS
*Acting Director of the United States Patent and Trademark Office*